United States Patent [19]
Au et al.

[11] Patent Number: 5,310,542
[45] Date of Patent: May 10, 1994

[54] ORAL HYGIENE COMPOSITIONS CONTAINING ANTIPLAQUE AGENTS

[75] Inventors: Van Au, Peekskill, N.Y.; Robert G. Carson, Rahway, N.J.; Bijan Harirchian, South Orange, N.J.; Kurt M. Schilling, Verona, N.J.

[73] Assignee: Lever Brothers Company, Division of Conopco, Inc., New York, N.Y.

[21] Appl. No.: 981,707

[22] Filed: Nov. 25, 1992

Related U.S. Application Data

[63] Continuation-in-part of Ser. No. 816,409, Dec. 31, 1991, abandoned.

[51] Int. Cl.$^5$ .................. A61K 31/70; A61K 6/00
[52] U.S. Cl. .................................. 424/52; 424/49; 424/54
[58] Field of Search ................... 424/49, 50, 52, 54

[56] References Cited

U.S. PATENT DOCUMENTS

| | | | |
|---|---|---|---|
| 2,746,916 | 5/1956 | Magariello | 204/79 |
| 2,752,334 | 6/1956 | Walton | 260/210 |
| 2,761,859 | 9/1956 | Hoffhine, Jr. | 260/210 |
| 2,785,152 | 3/1957 | Jonas | 260/112 |
| 4,137,397 | 1/1979 | Dutta et al. | 536/7.2 |
| 4,156,715 | 5/1979 | Wagenknecht et al. | 424/49 |
| 4,663,202 | 5/1987 | Causton | 424/54 |
| 4,665,060 | 5/1987 | Mardh et al. | 514/54 |
| 4,675,392 | 6/1987 | Dahmen et al. | 536/17.2 |
| 4,724,205 | 2/1988 | Karlsson et al. | 435/4 |
| 4,851,338 | 7/1989 | Mardh et al. | 514/58 |
| 4,855,128 | 8/1989 | Lynch et al. | 424/49 |
| 4,877,603 | 10/1989 | Degenhardt et al. | 424/52 |
| 4,992,420 | 2/1991 | Neeser | 514/8 |
| 4,994,441 | 2/1991 | Neeser | 514/8 |
| 5,002,759 | 3/1991 | Gaffar et al. | 514/54 |

FOREIGN PATENT DOCUMENTS

| | | |
|---|---|---|
| 0285178 | 10/1988 | European Pat. Off. |
| 2523962 | 9/1983 | France |
| 8205005 | 9/1983 | France |
| 3112904 | 5/1991 | Japan |
| 3112905 | 5/1991 | Japan |

| | | |
|---|---|---|
| WO92/05764 | 4/1992 | PCT Int'l Appl. |
| 2224204 | 5/1990 | United Kingdom |

OTHER PUBLICATIONS

Matsumura et al., *Journal American Oil Chemical Society*, vol. 67, No. 12 (Dec. 1990), pp. 996–1001.

Williams et al., *Carbohydrate Research*, vol. 67 (1978) pp. C1–C3.

Williams, Taffy J. et al. "A New Class of Model Glycolipids: Synthesis, Characterization, and Interaction with Lectins", *Archives of Biochemistry and Biophysics*, vol. 195, No. 1, (Jun. 1979), pp. 145–151.

Stromberg, Nicklas et al., Abstracts of International Association for Dental Research Scandinavian Division, Helsinki, Abstract Nos. 10 and 12 Aug. 22–24, 1991.

McIntire, Floyd C. et al. "Structural Preferences of $\beta$-Galactoside-Reactive Lectins on Actinomyces viscosus T14V and Actinomyces naeslundii WVU45", *Infection and Immunity*, vol. 41, No. 2, (Aug. 1983), pp. 848–850.

Stromberg, Nicklas et al. "Characterization of the Binding of Actinomyces naeslundii (ATCC 12104) and Actinomyces viscosus (ATCC 19246) to Glycosphingolipids, Using a Solid-phase Overlay Approach". *The Journal of Biological Chemistry*, vol. 265, No. 19 (Jul. 5, 1990), pp. 11251–11258.

Ziegast, Gerd et al. "Coupling of mono- and oligosaccharides to $\alpha$-w-diamino Substituted poly(oxyethylene) and Multifuncitional Amines by Amide Linkage". *Makromol. Chem., Rapid Commun.* vol. 5, (1984), pp. 373–379.

(List continued on next page.)

*Primary Examiner*—Ronald W. Griffin
*Attorney, Agent, or Firm*—Rimma Mitelman

[57] ABSTRACT

Dentifrice compositions including specific aldobionamides having a $\beta$-galactosidic linkage e.g., lactobionamides, which act as antimicrobial agents and/or inhibitors of bacterial adhesion.

29 Claims, No Drawings

OTHER PUBLICATIONS

Kolenbrander, Paul E. "Surface Recognition Among Oral Bacteria: Multigeneric Coaggregations and Their Mediators". Critical Reviews in Microbiology, vol. 17, Issue 2 (1989), pp. 137–159.

Gibbons, R. J. "Bacterial Adhesion to Oral Tissues: A Model for Infectious Diseases". Journal of Dental Research, vol. 68 No. 5, (May 1989), pp. 750–760.

Abstract of U.S. Patent Application Ser. No. 07/516463.

Abstract of Japanese Patent 55076811.

Abstract of U.S. patent application Ser. No. 07/349772.

Abstract of European patent application 0184121.

ORAL HYGIENE COMPOSITIONS CONTAINING ANTIPLAQUE AGENTS

This is a continuation-in-part of Ser. No. 07/816,409, filed Dec. 31, 1991, now abandoned.

FIELD OF THE INVENTION

The invention relates to oral hygiene compositions which inhibit formation and/or growth of bacteria responsible for dental plaque.

BACKGROUND OF THE INVENTION

An aldobionamide is defined herein as the amide of an aldobionic acid. The aldobionic acid is a sugar substance (e.g., any cyclic sugar) wherein the aldehyde group (generally found at the $C_1$ position of the sugar) has been replaced by a carboxylic acid. Aldobionamides are based on compounds comprising more than one saccharide unit; they may be based on compounds comprising two saccharide units (e.g., lactobionamide or maltobionamide) or they may be based on compounds comprising more than two saccharide units as long as the polysaccharide has a terminal sugar unit with an aldehyde group available for oxidation.

The inventive compositions include antiplaque agents which are specific aldobionamides containing at least one β-galactosidic linkage.

It is generally recognized that the development of dental plaque begins with the adhesion of bacteria to the teeth. Bacterial adhesion to tooth surfaces usually involves stereospecific interactions between cell surface binding proteins, referred to as adhesins, and cognate structures which form binding sites either in salivary pellicle, or on the surfaces of other bacteria resident in plaque, or in the extracellular plaque matrix (Gibbons, R. J.; J Dent Res 68, 750–760).

Many of the oral bacterial adhesins described in the art exhibit carbohydrate-specific binding and are often found on filamentous extensions (i.e., pili or fimbriae) which protrude from cell surfaces. These carbohydrate recognition structures, which are also referred to as lectins, mediate binding to host-derived or microbial-derived saccharide-containing structures on the teeth. Several different bacterial lectins have been described in the literature. By far, the lectins most commonly expressed by plaque bacteria are β-galactoside-specific or "lactose sensitive" adhesins. The genera of bacteria which produce β-galactoside-specific adhesins cover a diverse taxonomic range, including Actinomyces, Streptococcus, Porphyromonas, Fusobacterium, Haemophilus, Capnocytophaga, Veillonella, Prevotella, Staphylococcus, and Neisseria; these represent both primary and secondary colonizers of the teeth (Kollenbrander, P. E.; Crit Rev Microbiol 17:137–159). Kollenbrander notes that bacterial coaggregation plays an active role in formation of dental plaque and adherence of bacteria to epithelial cells in the oral econiche.

Most attempts to control plaque through anti-adhesion mechanisms have involved non-stereospecific inhibition of bacterial attachment to the teeth, usually with compositions containing surface-active polymers. For instance, G.B. Pat. No. 2,224,204A and U.S. Pat. No. 4,877,603 disclose oral compositions which include phosphonate-containing polymers that inhibit bacterial attachment to hydroxyapatite surfaces. Similarly, U.S. Pat. No. 4,663,202 discloses a method for treating surfaces with combinations of polymers which form barriers that retard bacterial adsorption.

With respect to blocking stereospecific interactions which mediate oral bacterial adherence, the use of mono- and oligosaccharides has been described, as inhibitors of lectin-mediated adhesion to human cells. For instance, abstract of U.S. Pat. No. 5,071,977 describes oligosaccharides isolated from *S. sanguis* which inhibit the build-up of adhesive dental plaque. Gaffar et al. (U.S. Pat. No. 5,002,759) disclose oligosaccharides containing either a galactose moiety (which may be β-galactose) and/or a fucose moiety as agents in dentifrice preparations for inhibiting adherence of *Streptococcus pyogenes* to human epithelial cells. European Patent Application 184,121 discloses the use of galactose and/or lactose as anti-caries agents in foods, drinks, and pharmaceutical preparations. Neeser (U.S. Pat. Nos. 4,992,420 and 4,994,441) describes kappa-caseinoglycopeptide compounds and desialylated derivatives thereof (the derivatives contain β-galactose groups) as inhibitors of in vitro adhesion by dental plaque bacteria to human erythrocytes.

Lynch et al. (U.S. Pat. No. 4,855,128) disclose polysaccharides such as xanthan gum, gum tragacanth, guar gum, gum karaya, chondroitin sulfate, polygalacturonic acid (pectin), sodium alginate and carrageenans of the kappa/lambda configuration as plaque-inhibitory agents which inhibit bacterial coaggregation; carrageenans of kappa/lambda configuration and chondroitin tin sulfate contain β-galactose.

Stromberg et a). (J. Biol. Chem. 265,11251–11258) disclose that N-acetyl-galactosamine-B1,3-galactose-O-ethyl is an inhibitor of binding by *Actinomyces viscosus* and *Actinomyces naeslundii* to human erythrocytes. McIntire et al. (Infection and Immunity, vol. 41, No. 2, 848–850) have described O-glycosides of galactose-B1,3-N-acetyl- galactosamine, including phenyl, phenylethyl, and nitrophenyl derivatives, which inhibit coaggregation between Actinomyces sp. and *Streptococcus sanguis;* McIntire et al. note that the addition of aglycones increased the inhibitory activity significantly but not greatly. Stromberg et al. ("Synthetic Receptoranalogues Prevent Plaque Formation in Man", Abstracts of International Association for Dental Research Scandinavian Division, Helsinki, Aug. 22–24, 1991) disclose a study demonstrating the plaque inhibitory activity of GalNAcβ-3Galα1-O-ethyl, which blocked adherence of Actinomyces strains 12104 and LY7. Clinical plaque strains were evaluated in a mouth rinse experiment including five human individuals. The study is said to demonstrate that receptor analogues such as GalNAcβ-3Galα1-O-ethyl, may prove useful in future antiplaque therapy. The glycosides described by the Stromberg and McIntire references are expensive molecules and are different to synthesize and purify; hence, their practical utility is limited to the study of the stereospecificity of bacterial binding.

Saccharide derivatives distinct from the compounds employed in the present invention have been disclosed for applications in a non-dental environment.

Abstracts of Japanese Patent Applications 03112905 and 03112904 disclose the use, as antibacterials for preserving food and cosmetics, of 2-acetylamino-N-alkyl-glycosylamines and alkyl-glycosyl-amines represented by structures 1 and 2, respectively. Mardh et al. (U.S. Pat. Nos. 4,851,338) disclose the use of glycosides of structure 3 (which may contain β-galactose) for diagnosing the presence of Staphylococcus bacteria and bacteria from the genus *Bordatella pertussis*.

STRUCTURE 1

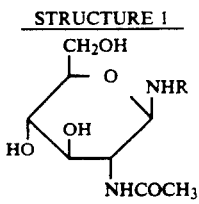

Wherein R is at least 8 carbon alkyl, preferably 12-18 carbons.

STRUCTURE 2

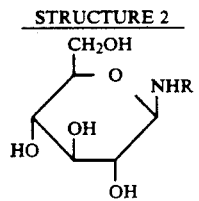

Wherein R is alkyl with at least 8 carbons

STRUCTURE 3

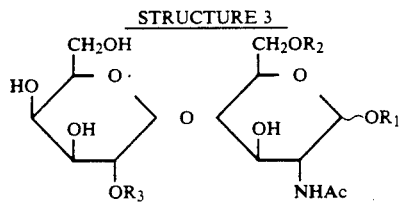

Wherein $R_1$, $R_2$ and $R_3$ are same or different and are hydrogen or an organic residue, for example lower alkyl, lower acyl, or a carbohydrate residue or an inorganic residue, such as sulphate or phosphate, and wherein $OR_1$ is α- or β-configuration.

Williams et al. ("A new class of Model Glycolipids: Synthesis, Characterization, and Interaction with Lectins", Archives of Biochemistry and Biophysics, vol. 195, No. 1 [1979], 145–151) disclose synthesis, characterization and lectin-glycolipid interaction of alkyl lactobionamides, cellobionamides and gentobionamides (all containing β-D-glycosidic linkages). The compounds contained alkyl chain lengths of 12 or more carbon atoms. Williams et al. note that the glycolipids are able to compete with monosaccharides for the carbohydrate binding site. The ability of the glycolipids to act as surfactants is discussed. The Williams article describes aldobionamide-induced agglutination of solubilized plant lectins which are not cell-associated. By contrast, compositions according to the present invention are not aimed at attaining agglutination but are meant to inhibit adherent interactions mediated by cell-associated lectins on oral bacteria and/or inhibit bacterial growth.

A concurrently filed commonly assigned application Ser. No. 07/816,409, now abandoned, discloses the general utility of nonionic aldonamides, including lactobionamides, as surfactants in personal products and detergent formulations. Oral hygiene compositions according to the present invention may include surfactant molecules taught by the concurrently filed application, but the present invention is based, in part, on the discovery that specific aldobionamides containing a β-galactosidic linkage, (e.g., lactobionamides) provide an antiplaque benefit by disrupting bacterial binding and/or acting as antimicrobial agents within the oral cavity.

Dental art heretofore has not made available a dentifrice composition containing antiplaque agents which are capable of delivering a surfactant benefit and/or antimicrobial activity and which also contain a β-galactose targeting group. Furthermore, there is need for relatively cheap antiplaque β-galactose-containing actives so that dentifrice compositions containing effective antiplaque agents may be produced on a commercial scale.

Accordingly, it is an object of the present invention to provide oral hygiene compositions which include specific aldobionamides containing a β-galactosidic linkage as antiplaque agents.

It is another object of the present invention to provide oral hygiene compositions which contain effective yet commercially feasible antiplaque β-galactose-containing compounds.

It is still another object of the invention to provide methods of inhibiting bacterial adhesion and/or bacterial growth in the oral cavity.

These and other objects of the invention will become more apparent from the detailed description and examples that follow.

SUMMARY OF THE INVENTION

The above objects are accomplished by the present invention which includes oral hygiene compositions containing an effective plaque-inhibiting amount of at least one compound selected from the group consisting of an aldobionamide, a corresponding ammonium salt of the aldobionic acid and mixtures thereof, wherein the compound includes (i) at least one β-galactosidic linkage and (ii) an amide group:

wherein $R^1$ and $R^2$ are the same or different and are selected from the group consisting of hydrogen, an aliphatic hydrocarbon radical, an aromatic radical, a cycloaliphatic radical, an amino acid ester and mixtures thereof. $R^1$ and $R^2$ may include heteroatoms, i.e. N, O, and S, present for instance as an amide, carboxy, ether, and/or saccharide moieties.

Aldobionamides are carbohydrate-based molecules and, thus, represent a source of renewable raw materials that are synthetically versatile and environmentally friendly. Preferred antiplaque agents are lactobionamides of Formula A due to their low cost. Lactobionamides may be produced from lactobiono-1,5-lactone which is produced from lactobionic acid which, in turn, is obtained from lactose. Compared to other naturally occurring disaccharides, lactose is cheap and its supply is abundant. Consequently, production of large quantities of dentifrice compositions containing various lactobionamides is particularly attractive from the commercial standpoint. The corresponding ammonium salts of lactobionic acid are represented by formula B.

FORMULA A

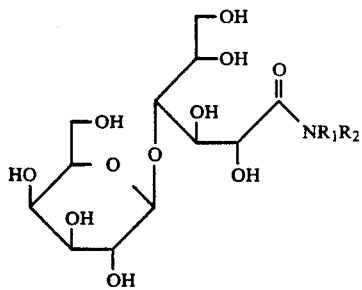

FORMULA B

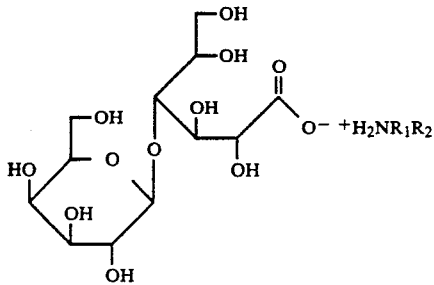

Preferred lactobionamides include but are not limited to N-alkyl lactobionamides, N-lactobionyl amino acid esters, and N-(alkyloxy)alkyl lactobionamides.

Of course, other aldobionamides containing a β-galactosidic linkage may be employed.

The inventive dental compositions incorporate aldobionamides which, singly or in combination with each other, provide enhanced inhibition of bacterial aggregation, surfactancy, and antimicrobial activity. The inventive compositions inhibit adhesion and/or growth of bacteria responsible for dental plaque, thereby preventing the plaque formation, plaque-induced diseases, calculus formation, dental caries, gingivitis, and periodontal disease.

The compositions of the present invention may be in the form of toothpastes, mouthwashes, rinses, tooth powders, gels, dental flosses, chewing gums, and lozenges, as well as other oral delivery vehicles.

The invention also includes methods of inhibiting plaque formation and growth which include applying the inventive compositions into the oral cavity.

DETAILED DESCRIPTION OF THE INVENTION

Oral hygiene compositions of the invention include as an essential ingredient at least one aldobionamide compound containing a β-galactosidic linkage. The aldobionamide may be based on a compound comprising two saccharide units, e.g. lactobionamide, or they may be based on compounds comprising more than two saccharide units, such as trisaccharides and oligosaccharides, as long as at least one β-galactosidic linkage is present. In particular, the inventive compositions include at least one antiplaque compound selected from the group consisting of an aldobionamide, a corresponding ammonium salt of the aldobionic acid, and mixtures thereof, wherein the compound includes (i) at least one β-galactosidic linkage and (ii) an amide group:

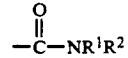

wherein $R^1$ and $R^2$ are the same or different and are selected from the group consisting of hydrogen, an aliphatic hydrocarbon radical, an aromatic radical, a cycloaliphatic radical, an amino acid ester and mixtures thereof. $R^1$ and $R^2$ may include heteroatoms, i.e. N, O, and S, present for instance as an amide, carboxy, ether, and/or saccharide moieties.

Preferred compounds are derived from lactobionic acid, due to its ready availability and low price.

Preferably, in order to simplify synthesis and reduce cost of the active compounds, $R^1$ is hydrogen.

N-alkyl lactobionamides are compounds of Formula A wherein $R^1$ and/or $R^2$ is an aliphatic hydrocarbon radical (which may include heteroatoms). Suitable aliphatic hydrocarbon radicals include saturated and unsaturated radicals including but not limited to methyl, ethyl, amyl, hexyl, heptyl, nonyl, decyl, undecyl, dodecyl, tridecyl, tetradecyl, pentadecyl, hexadecyl, heptadecyl, and octadecyl, and allyl, undecenyl, oleyl, linoleyl, linolenyl, propenyl, and heptenyl. The active compounds of the inventive compositions may contain straight or branched aliphatic groups. Aromatic radicals are exemplified by benzyl, aniline, or substituted benzyl or aniline groups. Suitable mixed aliphatic aromatic radicals are exemplified by benzyl, phenyl ethyl, phenoxy ethyl, and vinyl benzyl. Cycloaliphatic radicals are exemplified by but not limited to cyclopentyl and cyclohexyl.

N-lactobionyl aminoacid esters include but are not limited to esters of those amino acids which naturally occur in proteins, e.g., alanine, valine, glycine, lysine leucine, arginine, aspartic acid, glutamic acid, asparagine, glutamine, threonine, serine, cysteine, histidine, tyrosine, methionine, as well as naturally occurring amino acids which are not found in proteins, such as β-alanine, sarcosine gamma-aminobutyric acid, ornithine, citrulline, and the like. An example of N-lactobionyl amino acid ester is when in Formula A $R^1$ is hydrogen and $R^2$ is

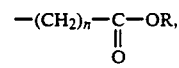

where n is an integer greater than 1 and R is for instance an aliphatic hydrocarbon radical containing up to 36 carbon atoms.

N-(alkyloxy)alkyl lactobionamides are exemplified but not limited to compounds wherein $R^1$ and/or $R^2$ is $—(CH_2)_n—O—R^6$, wherein n is an integer equal to or greater than 1, preferably from 1 to 10 and $R^6$ is an aliphatic hydrocarbon radical, an aromatic radical, a cycloaliphatic radical as described above for $R^1$ and $R^2$. Preferably n is from 1 to 3 and $R^6$ is an aliphatic hydrocarbon radical containing 1 to 18 carbon atoms.

N-alkyl lactobionamides, N(alkyloxy)alkyl lactobionamides and N-lactobionyl aminoacid esters typically contain up to 36 carbon atoms in $R^1$ and $R^2$ groups, preferably up to 24 carbon atoms, most preferably from 8 to 18 carbon atoms, and optimally from 8 to 16 carbon atoms in order to attain optimum surface activity.

N-(polyalkyloxy)alkyl lactobionamides are exemplified by but not limited to compounds wherein $R^1$ and- /or $R^2$ is $-R^4-(OR^4)_n-R^4-R^5$ wherein n is an integer greater than 1, $R^4$ is selected from the group consisting of ethylene, propylene, and mixtures thereof; and $R^5$ is an amine or lactobionamide moiety. The number of repeating units in the alkylene oxide radical typically ranges from 2 to 10,000, preferably is from 2 to 100, most preferably from 2 to 10. $R^5$ is preferably lactobionamide (the resulting compound is N-(polyalkyloxy)alkyl (bis) lactobionamide, e.g., N-(polyethylene oxide) bis lactobionamide) in order to provide an additional β-galactose moiety. $R^1$ and/or $R^2$ groups within N-(polyalkyloxy)alkyl lactobionamides may contain heteroatoms; for instance, $R^2$ may be $-CH_2CH_2-S-CH_2CH_2-(OCH_2OCH_2)_n-S-CH_2CH_2-R^5$.

Of course other $R^1$ and $R^2$ radicals not listed above but within the scope of the invention may be employed. Likewise, other aldobionamides may be employed as long as a β-galactosidic linkage is present.

All of the above-described compounds may be in the form of the corresponding ammonium salt as represented above by Formula B.

The aldobionamides may be suitably prepared from aldobionolactone, preferably aldobiono-1,5-lactone, and a requisite organic primary or secondary amine carrying the desired $R_1$ and $R_2$ chains.

The preferred methods of preparation are disclosed in Ser. No. 07/816,422, now abandoned and Ser. No. 07/958,402 commonly assigned patent applications, incorporated by reference herein, which describes the synthesis of N-substituted aldobionamides by the reaction (25°-65° C.) of aldobionolactone with various primary or secondary amines. The example of the reaction is as follows:

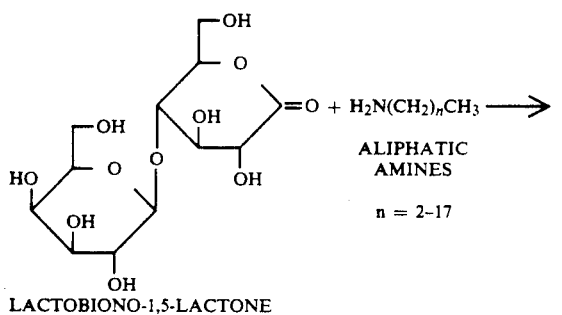

LACTOBIONO-1,5-LACTONE

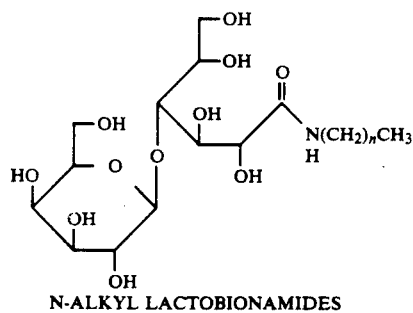

N-ALKYL LACTOBIONAMIDES

Aldobionolactones may be obtained commercially, (e.g., from Aldrich Chemicals) or they may be prepared by dissolving an aldobionic acid in an organic solvent such as dioxane or methanol. Preparation of aldobionolactones is described in a greater detail by Williams et al., "A new Class of Glycolipids: Synthesis, Characterization, and Interaction with Lectins," Archives of Biochemistry and Biophysics, Vol. 195, No. 1, June, 145-151, 1979 and by H. S. Isbell, Bureau of Standards, Journal of Research, Vol. 11, 1933 which disclosures are incorporated by reference herein. Alternatively, aldobionolactones may be obtained by spray drying an aqueous solution as described in U.S. Pat. No. 2,746,916, incorporated by reference herein. An aldobionolactone preferably employed in the present invention is an aldobiono-1,5-lactone.

The amine, HNR1R2 may be obtained commercially (Aldrich Chemicals) as in the case of aliphatic amine, or from Sherex as in the case of (oxyalkyl)alkyl amine (Adogen 180®) or they may be synthesized. When aliphatic amines are employed $R^1$ and/or $R^2$ contain at least 3 carbon atoms to ease synthesis (amines wherein $R^1$ and/or $R^2$ are fewer than 3 carbon atoms have to be bubbled in due to their high volatility).

In the preferred method, the molar ratio of the aldobionolactone to the amine in the starting reaction mixture is in the range of from 1:1.5 to 1:1. Preferably, an equimolar ratio is employed.

The preferred method includes recovering the by-product of the reaction, a corresponding ammonium salt of an aldobionic acid (which in the case of lactobionamides is represented by general Formula B), which may itself be used as an active ingredient of the inventive compositions. The solution containing the by-product may be passed through an anionic exchange column to convert the ammonium salt into the starting amine. The aldobionate anion is retained on the column and may be converted into the salt of aldobionic acid by washing the column with base and eluting with distilled deionized water. The salt may then be converted into the aldobionic acid which in turn may be converted into the starting lactone. The preferred method results in an improved yield and allows for a continuous process.

The preferred method may be employed for preparation of any aldobionamides included in the inventive compositions. However, since the inventive compositions may include the ammonium salt of aldobionic acid, it is not necessary to separate the aldobionamide from the salt: both the main product, aldobionamide, and the by-product, the ammonium salt, are suitable for inclusion in the inventive compositions, and the mixture containing both may be employed.

Alternative methods of synthesis are available.

N-alkyl lactobionamides may be prepared as described in U.S. Pat. No. 2,752,334, which is incorporated by reference herein.

The preparation of N-lactobionyl amino acid esters is described in U.S. Pat. No. 2,785,152, incorporated by reference herein. The preparation of N-(alkyloxy)alkyl lactobionamides is described in the article by Ziegast (Makromol. Chem., Rapid Commun. 5, 373-379 (1984)), which is incorporated by reference herein.

Ammonium salts of the aldobionic acid may be prepared as described in U.S. Pat. No. 4,137,397 and U.S. Pat. No. 2,761,859, both of which are incorporated by reference herein. Preferably, the process disclosed in the '397 and '859 patents is modified by employing higher temperature (about 70° C.) to facilitate the formation of lactobionic acid from lactobiono-1,5-lactone and to aid the dissolution of the alklyamines in the aqueous solution. Also, low boiling methanol was used instead of ethanol or acetone employed in the '397 and '859 patents.

The aldobionamide compounds containing a β-galactosidic linkage and specific $R^1$ and $R^2$ groups as described above are capable of delivering various antiplaque benefits. It has been found that lower chain alkylaldobionamides (number of carbon atoms $R^1$ and $R^2$ chains less than 14, preferably less than 10), N-aldobionyl amino acid esters, and N-(alkyloxy)alkyl aldobionamides are particularly effective in preventing bacterial adherent interactions. N-aldobionyl amino acid esters and higher chain (preferably at least 8 carbon atoms) alkyl aldobionamides are also effective antimicrobial agents (in addition to their bacterial anti-adhesion properties and their surfactant activity).

The aldobionamide compounds are employed in the present invention in an amount effective to inhibit plaque formation. The amount depends on the particular compound employed, but ranges generally from about 0.0001% to about 20%, preferably from about 0.001% to about 10%, and most preferably from about 0.01% to about 5%, by weight of the final composition.

It is also preferred that the aldobionamides are water-soluble in order to ease the formulation, particularly of toothpaste and mouthwash compositions, and to increase the diffusibility of the amino sugars into plaque matrix.

The preferred oral compositions of the present invention are in the form of toothpaste, dental cream, gel or tooth powder, as well as mouthwash, pre-brushing rinse, or post-brushing rinse formulations, chewing gums and lozenges.

Ingredients typically included in toothpastes and gels may be used in toothpaste and gel compositions in accordance with the invention. Suitable ingredients include abrasive polishing materials, sudsing agents, flavoring agents, humectants, binders, sweetening agents, and water.

Mouthwashes are typically comprised of a water/alcohol solution, flavor, humectant, sweetener, foaming agent, and colorant.

Abrasives which may be used in the compositions of the invention include alumina and hydrates thereof, such as alpha alumina trihydrate, magnesium trisilicate, magnesium carbonate, aluminosilicates, such as calcined aluminum silicate and aluminum silicate, calcium carbonate, zirconium silicate, polymethyl methacrylate, powdered polyethylene, silica xerogels, hydrogels and aerogels and the like. Also suitable as abrasive agents are calcium pyrophosphate, insoluble sodium metaphosphate, calcium carbonate, dicalcium orthophosphate, particulate hydroxyapatite and the like. Depending on the form which the oral composition is to take, the abrasive may be present in an amount of from 0 to 70% by weight, preferably 1 to 70% by weight, more preferably from 10 to 70% by weight, particularly for toothpastes.

Humectants contemplated for use in the present invention include glycerol, polyol, sorbitol, polyethylene glycols, propylene glycol, hydrogenated partially hydrolyzed polysaccharides and the like. The humectants are generally present in amounts of from 0 to 80%, preferably 5 to 70% by weight, particularly for toothpastes. Thickeners suitable for use in the invention include silica. Thickeners may be present in toothpaste creams and gels at 0.1 to 20% by weight.

Binders suitable for use in the compositions of the invention include hydroxyethyl cellulose (Natrosol ®), sodium carboxymethyl cellulose and hydroxypropyl cellulose (Klucel ®), as well as xanthan gums, Irish moss and gum tragacanth. Binders may be present in the toothpaste of the invention to the extent of from 0.01 to 10%. Sweeteners suitable for use in the present dentifrice, preferably at levels of about 0.1% to 5%, include saccharin.

Suitable foaming agents include soap, anionic, cationic, nonionic, amphoteric and/or zwitterionic surfactants. These may be present at levels of 0 to 15%, preferably 0.1 to 15%, more preferably 0.25 to 10% by weight. It should be noted that many of the glycoside-surface active agents described in the present invention also may be used as foaming agents at concentrations ranging from 0 to 15% by weight.

Certain pyrophosphate and other polyphosphate salts have been disclosed in U.S. Pat. Nos. 4,515,772 and 4,627,977 as being useful as anti-calculus agents. These include di- and tetra-alkali metal pyrophosphates wherein the alkali metals are preferably selected from the group consisting of sodium and potassium. Polyphosphate salts may be included generally in the amount such that it provides for at least 0.5% polyphosphate anions, the upper level being about 10%, preferably about 7.5%.

Various anionic polymers may be employed as anticalculus and/or antiplaque agents. Suitable polymers include carboxylate polymers, sulfonate polymers, polymers containing a sulfonate and a carboxylate moiety, carboxylate polymers containing phosphinate units, and mixtures thereof. The carboxylate polymers suitable in the present compositions are described by Gaffar et al., U.S. Pat. No. 4,808,400, incorporated by reference herein. Suitable carboxylate polymers containing mono- or disubstituted hypophosphite units along the polymer backbone are described in a U.S. Pat. No. 5,011,682 incorporated by reference herein. The anionic polymers may be included at a level from about 0.01 to about 10%, preferably from about 0.05 to about 5%.

Zinc salts are disclosed as anti-calculus and antiplaque agents in U.S. Pat. No. 4,100,269 and in U.S. Pat. Nos. 4,416,867, 4,425,325 and 4,339,432. preferred compositions of the invention include zinc salts, particularly zinc citrate. The zinc compounds may be present in the compositions in amounts sufficient to furnish about 0.01% to about 4% zinc, or preferably about 0.05% to about 1%, zinc ion.

Fluoride sources used in toothpastes such as sodium fluoride, stannous fluoride, sodium monofluorophosphate, zinc ammonium fluoride, tin ammonium fluoride, calcium fluoride and cobalt ammonium fluoride may be, and preferably are, included for delivering anti-caries benefit. Preferred compositions of the invention include the fluoride source. Fluoride ions are typically provided at a level of from 0 to 1500 ppm, preferably 50 to 1500 ppm, although higher levels up to about 3000 ppm may be used.

Flavors are usually included in toothpastes in low amounts, such as from 0.01 to about 5% by weight, especially from 0.1% to 5%.

Water-soluble antibacterial agents, such as chlorhexidine digluconate, hexetidine, alexidine, quaternary ammonium anti-bacterial compounds and water-soluble sources of certain metal ions such as zinc, copper, silver and stannous (e.g., zinc, copper and stannous chloride, and silver nitrate) may also be included.

Titanium dioxide is a suitable whitener.

Dyes/colorants suitable for dentifrices, i.e., FD&C Blue #1, FD&C Yellow #10, FD&C Red #40, etc., may be employed in the dentifrices of the invention.

Various other optional ingredients may be included in the compositions of the invention, such as preservatives, vitamins such as vitamin C and E, other anti-plaque agents such as stannous salts, copper salts, strontium salts and magnesium salts. Also included may be pH adjusting agents, anti-caries agents such as urea, calcium glycerophosphate, sodium trimetaphosphate, silicone polymers, plant extracts, desensitizing agents for sensitive teeth such as potassium nitrate and potassium citrate, and mixtures thereof.

Casein and/or its hydrolysate may be included as anticaries agents, e.g. at a level of 0.01 to 20% by weight, preferably 0.1 to 10%.

The corresponding compounds mentioned above which are used in toothpastes, are generally suitable within the ranges above for mouthwashes as well. The mouthwash can include ethanol at a level of from 0 to 60%, preferably from 5 to 30% by weight.

The following specific examples further illustrate the present invention, but the invention is not limited thereto.

METHODS

Bacterial Coaggregation Assay

A bacterial coaggregation assay was used to determine the ability of various amino sugars to interfere with lectin-mediated binding among various bacterial species. For instance, many *Actinomyces naeslundii* strains coaggregate with *Streptococcus sanguis* as a result of binding between a lectin produced by the *A. naeslundii* cells and β-galactose-containing structures on the surface of the streptococci. For the present assay, *A. naeslundii* PK29 and *S. sanguis* G9B were cultured overnight in a medium containing 2.5% tryptone, 1.5% yeast extract, 0.1% magnesium sulfate, and 1.0% fructose. The cells were then washed twice in a 1.0 mM potassium phosphate buffer (pH=6.8) containing 1.0 mM calcium chloride, 0.1 mM magnesium chloride, and 50.0 mM potassium chloride (buffered KCl), after which they were resuspended in buffered KCl at an optical density (540 nm) of 1.5. The coaggregations were performed by combining 0.5 ml of each bacterial suspension with 0.2 ml of 5.0% bovine serum albumin (BSA) and 0.8 ml of an appropriate concentration of a targeted anti-plaque agent in 3.0 ml capped polystyrene cuvettes. The cuvettes (path length 1 cm) were gently inverted at room temperature, and the optical density (540 nm) was determined as a function of time (2.0 min intervals; 20 min). The instrument employed to measure optical density was a variable wavelength spectrophotometer (Gilson Response ® Spectrophotometer, bought from Gilson).

The activity of a tested compound was expressed as % inhibition relative to buffer controls (i.e., % inhibition = [1 − change in optical density (inhibitor)]/change in optical density [control]) × 100.

Latex Bead-Bacterial Agglutination Assay

A latex bead agglutination assay was utilized to determine the effects of the amino sugars on lectin-mediated bacterial adherence to glycoprotein-coated surfaces. Latex beads (6.0 micrometer diameter) were prepared by suspending them in a 0.5 mg/ml solution of asialofetuin (a glycoprotein rich in oligosaccharide side chains which terminate in β-galactosyl groups) in 20.0 mM trishydroxyaminomethane buffer (pH=8.2) containing 0.73% glycine, 1.0% sodium chloride, 0.1 mM calcium chloride, and 0.02% sodium azide (TGS buffer). The beads were treated for 30.0 min at 37 degrees C. after which they were washed and resuspended in 0.1% BSA in TGS buffer. *A. naeslundii* pK29 cells were cultured as described in Bacterial Coaggregation Assay, washed, and resuspended in TGS buffer to an optical density (540 nm) of 1.5. The bacterial suspension (0.1 ml) and the prepared latex beads (1.0 ml) were combined with an appropriate concentration of inhibitor (0.8 ml) in 3.0 ml capped polystyrene cuvettes. The cuvettes were gently inverted at room temperature, and optical density (OD 540 nm, 1 cm path length) was monitored at 2.0 min intervals for 20.0 min. The instrument employed was Gilson Response ®.

Antimicrobial Activity Determination

The antimicrobial activity of the targeted agents was assessed by determining the minimum inhibitory concentration (MIC). Pure cultures of various strains of oral bacterial species as indicated in Table 3 were combined with serial dilutions of the targeted agents in beef heart infusion broth (BHI); starting bacterial concentrations were approximately $1.0 \times 10E6$ colony forming units (CFU) per ml. The mixtures were incubated aerobically at 37 degrees C. and the optical density (540 nm, path length 1 cm) of the cultures was measured at 0.0, 24.0 and 48.0 hr using Bausch and Lomb Spec 20 variable wavelength spectrophotometer.

EXAMPLE 1

Various aldobionamides suitable for use in the inventive compositions, were prepared.

N-propyl lactobionamide 5 g (1 eq) of lactobiono-1,5-lactone was dissolved in 20 ml of anhydrous DMF at 80 degrees C., and 0.86 g (1 eq) of propylamine was added. The reaction was stirred at 80 degrees C. for 30 min. The solvent was removed, and the residue was washed twice with ethyl ether. Recrystallization from MeOH/ethyl ether gave an 80% yield of N-propyl lactobionamide.

N-pentyl lactobionamide

A mixture of 5 g (1 eq) of lactobiono-1,5-lactone and 1.41 g (1 eq) of amylamine was heated in 30 ml of anhydrous MeOH to reflux for one hour. A small amount of activated charcoal was added, and the mixture was filtered hot. The solvent was removed, and the residue was washed with ethyl ether, followed by an acetone wash, and then was dried. N-pentyl lactobionamide was obtained in a 60% yield

N-octyl lactobionamide

A mixture of 10 g (1 eq) lactobiono-1,5-lactone and 7.6 g (1 eq) of octylamine was heated to 90° C. for 30 min with vigorous stirring. The reaction was allowed to cool, and the residue was washed with ethyl ether. Recrystallization twice with MeOH/ethyl ether gave an 80% yield of N-octyl lactobionamide.

N-decyl lactobionamide 20 g (1 eq) of lactobiono-1,5-lactone was dissolved in 40 ml of anhydrous DMF at 75°–80 degrees C., 8.8 g (1 eq) of decylamine was added. The reaction was maintained at 75°–80° C. with stirring for 30 min, after which it was cooled, 150 ml of ethyl ether was added, and the product was filtered. After washing twice with ethyl ether, N-decyl lactobionamide was recrystallized twice in MeOH/ethyl ether to give a 80% yield.

N-dodecyl lactobionamide 30 g (1 eq) of lactobiono-1,5-lactone was dissolved in 70 ml of anhydrous DMF at 75°-80° C., and 15.85 g (1 eq) of dodecylamine was added. The reaction was maintained at 70°-80° C. for 30 min, after which the reaction was cooled, diluted with 200 ml ethyl ether, and filtered. The product was washed twice with ethyl ether, and the N-dodecyl lactobionamide was recrystallized from MeOH to give a 90% yield.

Alternatively, 20 g (1 eq) of lactobiono-1,5-lactone and 11 g (1 eq) of dodecylamine were dissolved in MeOH by heating it to reflux temperature. The reaction mixture was allowed to stir at room temperature overnight, after which the product was filtered, washed with MeOH, and then washed with ethyl ether. Recrystallization of N-dodecyl lactobionamide with MeOH gave a 57% yield.

N-tetradecyl lactobionamide 20 g (1 eq) of lactobiono-1,5-lactone was dissolved in 60 ml of anhydrous DMF at 65° C.; 12.5 g (1 eq) of tetradecylamine was added, and the reaction was stirred for 30 min. The reaction mixture was cooled, filtered after adding ethyl ether, and washed in ethyl ether. Recrystallization of N-tetradecyl lactobionamide with MeOH gave a 92% yield.

N-hexadecyl lactobionamide

The same procedure was used as for N-tetradecyl lactobionamide except that 10 g (1 eq) of lactobiono-1,5-lactone was added to 7.1 g (1 eq) of hexadecylamine. Recrystallization from MeOH resulted in a yield of 90%.

N-lactobionyl dodecyl glycinate

Preparation of dodecyl glycinate hydrochloride: 20 grams of glycine methyl ester hydrochloride (supplied by Aldrich), 130 grams of dodecyl alcohol (Aldrich) and sulfuric acid (1 ml) were heated at 95° C. under aspirator vacuum for 14 hours. Hexane (500 ml) was added and the mixture was filtered when hot. Upon cooling, dodecyl glycinate hydrochloride was collected by filtration, washed with acetone and dried in vacuum oven. The yield was 40 grams.

9.0 g dodecyl glycinate hydrochloride was dissolved in 50 ml of anhydrous methanol by gentle heating, 16 ml of 2.0M methanolic ammonia was added, followed by addition of 10.9 g (1 eq) of lactobiono-1,5-lactone. The reaction mixture was heated to reflux for 2.0 hours, activated was charcoal was added and the mixture was filtered hot. The solvent was removed, the product was washed with ethyl ether and dried in a vacuum oven at 40° C. over $P_2O_5$. The product yield of approximately 75%.

N-lactobionyl dodecyl β-alanate

The analogous procedure as described above for the synthesis of N-lactobionyl dodecyl glycinate was employed. The yield was approximately 70%.

Preparation of butyl-1,4-bis-lactobionamide

Lactobiono-1,5-lactone (20 g, 1 eq) was dissolved in methanol (200 ml, 50° C.). 1,4-diaminobutane (2.6 g, 1 eq) was added. The resulting mixture was stirred at 50° C. for one hour. The resulting reaction mixture was filtered, the filtrate was eluted through a column containing anionic exchange resin. The solvent was removed, the residue was washed with warm acetone and dried in vacuum oven at 40° C. The yield was 10.1 g.

Preparation of coco lactobionamide

Lactobiono-1,5-lactone (400 g, 1 eq) was dissolved in methanol (2.3 l, 50° C.) with stirring, cocoamine (Adogen 160-D ®,211.8 g, 1 eq) was added slowly over 10 minutes. After the addition was completed, the reaction mixture was stirred for additional 10 minutes followed by seeding the solution with small amount of coco lactobionamide. The resulting mixture was stirred overnight at room temperature. The product was filtered, washed with with warm acetone twice and dried in vacuum oven at 40° C. The yield was 394 g.

Preparation of dodecyl oxypropyl lactobionamide

Lactobiono-1,5-lactone (180 g, 1 eq) was dissolved in methanol (50° C., 1.11 l). Dodecyl oxypropylamine (115.8 g, 1 eq) was added slowly. After the addition was completed, the reaction mixture was stirred overnight at room temperature. The product was filtered, washed with warm acetone twice and dried in vacuum oven at 40° C. The yield was 215 g.

Preparation of tetradecyl oxypropyl lactobionamide

Lactobiono-1,5-lactone (500 g, 1 eq) was dissolved in methanol (50° C., 3 l). Tetradecyl oxypropylamine (Adogen 184 ®, 385 g, 1 eq) was added in several portions, slowly. After the addition was completed, the reaction mixture was stirred at room temperature overnight. The product was filtered, washed with warm acetone twice and dried in vacuum oven at 40° C. The yield was 647 g.

Preparation of oleyl lactobionamide

Lactobiono-1,5-lactone (100 g, 1 eq) was dissolved in methanol (50° C., 400 ml) oleylamine (Adogen 172-D ®,76.1 g, 1 eq) was added slowly. After the addition was completed, the reaction mixture was stirred at room temperature overnight. The product was filtered, washed with acetone twice and dried in vacuum oven at 40° C. The yield was 130 g.

Preparation of N-dodecyl-N-methyl lactobionamide

Lactobiono-1,5-lactone (8.7 g, 1 eq) was dissolved in methanol (50° C., 30 ml) N-dodecylmethylamine (5 g, 1 eq) was added. The reaction was stirred overnight at room temperature. The solvent was removed, the product Was washed with ethanol followed by washing with acetone and dried in vacuum oven at 40° C. The yield was 12 g.

Preparation of tallow lactobionamide

Lactobiono-1,5-lactone (200 g, 1 eq) was dissolved in methanol (45° C., 1.3l) tallow amine (Adogen 170-D ®, 144.7 g, 1 eq) was added slowly in several portions. After the addition completed, the reaction mixture was stirred overnight at room temperature. The product was filtered, washed with isopropanol followed by washing with acetone and dried in vacuum oven at 40° C. The yield was 270 g.

Dodecylammonium lactobionate

Lactobiono-1,5-lactone (13.2 g, 1 eq) was dissolved in water (150 ml) at 70° C.; dodecyllamine (7.2 g, 1 eq) in 50 ml MeOH was added slowly. The resulting solution was rotary evaporated to remove MeOH, followed by freeze-drying to give 20 g of dodecylammonium lactobionate.

Tetradecylammonium lactobionate

Lactobiono-1,5-lactone (20 g, 1 eq) was dissolved in water (150 ml) at 70° C. Tetradecylamine (12.5 g, 1 eq) in 50 ml of methanol was added dropwise. The resulting solution was evaporated on a rotary evaporator to remove methanol. The resulting mixture was freeze-dried to give 30 grams of tetradecylammonium lactobionate.

Hexadecylammonium lactobionate

Lactobiono-1,5-lactone (5.0 g, 1 eq) was dissolved in water (75 ml) at 70° C.; hexadecylamine (3.1 g, 1 eq) in 30 ml of MeOH was added slowly. The resulting mixture was stirred for 4.0 hr, rotary evaporated, and freeze-dried to give 7.5 g of hexadecylammonium lactobionate.

EXAMPLE 2

The ability of various aldobionamide compounds (prepared as described in Example 1) to target to $\beta$-galactose-specific binding proteins on *A. naeslundii* and thus to interfere with coaggregation interactions between *A. naeslundii* and *S. sanguis* was investigated. Coaggregation of *Actinomyces naeslundii* PK29 and *Streptococcus sanguis* G9B was performed as described in the Methods section (Bacterial Coaggregation Assay) above. % Inhibition was calculated as 1.0−the change in optical density (540 nm) in the sample containing compound tested/the change in optical density in the coaggregation buffer control. The inhibitory activity of the antiplaque agents within the scope of the invention was compared to the inhibitory activity of lactobionic acid and N-alkyl gluconamides, which are not within the scope of the invention. The gluconamides were prepared analogously to N-alkyl lactobionamides from glucono-δ-lactone (Sigma Chemicals) and the requisite aliphatic amine. The results that were obtained are summarized in Table 1.

TABLE 1

Inhibition of coaggregation of *Actinomyces naeslundii* and *Streptococcus sanguis* by various aldobionamide compounds

| # | Compound Tested | Concentration | % Inhibition |
|---|---|---|---|
| 1 | N-propyl lactobionamide | 2.5 mMol/L | 16% |
|   |   | 5.6 mMol/L | 50% |
| 2 | N-pentyl lactobionamide | 2.3 mMol/L | 18% |
|   |   | 5.6 mMol/L | 54% |
| 3 | N-octyl lactobionamide | 5.6 mMol/L | 47% |
| 4 | N-hexadecyl lactobionamide | 0.2 mMol/L | 0.2% |
|   |   | 0.4 mMol/L | 81% |
|   |   | 0.9 mMol/L | 82% |
| 5 | O-dodecyl-N-β-alanyl-lactobionamide | 0.8 mMol/L | 0.0% |
|   |   | 1.7 mMol/L | 56% |
|   |   | 2.5 mMol/L | 68% |
| 6 | 1,4-Diaminobutyl-Bis-lactobionamide | 1.4 mMol/L | 55% |
|   |   | 2.8 mMol/L | 72% |
| 7 | Lactobionic acid | 2.8 mMol/L | 20% |
|   |   | 5.6 mMol/L | 46% |
| 8 | N-heptyl gluconamide | 1.7 mMol/L | 0.0% |
|   |   | 3.4 mMol/L | 0.8% |
| 9 | N-decyl gluconamide | 1.5 mMol/L | 0.0% |
|   |   | 3.0 mMol/L | 0.9% |

As can be seen from Table 1 the inhibitory activity of some targeted anti-plaque agents is equal to or greater than the activity observed for lactobionic acid.

Lower chain alkyl lactobionamides and N-aldobionyl amino acid esters proved to be potent inhibitors of bacterial coaggregation. As shown in Table 1, O-dodecyl-N-β-alanyl lactobionamide had markedly better inhibitory activity against β-galactose-specific coaggregation than did lactobionic acid. N-aldobionyl amino acid esters are also effective antimicrobial agents (See Example 6).

In addition, the bacterial coaggregation assay was carried out with N-decyl lactobionamide, N-dodecyl lactobionamide, and N-tetradecyl lactobionamide, for which compounds poor inhibitory activity was observed; however, qualitative secondary effects (e.g., reversible adsorption of the bacteria to cuvette walls, differences in size and appearance of bacterial aggregates) suggest that interactions between these lactobionamide surfactants and bacteria do occur.

In addition, the coaggregation assay was inappropriate for testing N(polyethylene oxide) bis lactobionamide since this compound induces slight agglutination of *A. naeslundii* leading to enhanced coaggregation. However, as demonstrated by Example 3, N(polyethylene oxide) bis lactobionamide is a potent inhibitor of adhesion of *A. naeslundii* to glycoprotein coated surfaces.

EXAMPLE 3

The ability of aldobionamides to inhibit bacterial adhesion was also tested using the latex bead assay described above. This assay measures the ability of the test agents to interfere with bacterial adhesion to a glycoprotein-coated solid surface. The test is more suitable for examining the higher alkyl chain length aldobionamides than the bacterial coaggregation assay. The results that were obtained are summarized in Table 2.

TABLE 2

Inhibition of Bacterial-Latex Bead Agglutination by Lactobionamides*

| Inhibitor | Concentration | % Inhibition |
|---|---|---|
| Lactobionic acid | 2.3 mMol/L | 2.7% |
|   | 3.9 mMol/L | 5.8% |
|   | 11.3 mMol/L | 10.9% |
| N-propyl lactobionamide | 2.3 mMol/L | 6.7% |
|   | 11.7 mMol/L | 21.1% |
| N-pentyl lactobionamide | 2.3 mMol/L | 5.5% |
|   | 11.7 mMol/L | 26.9% |
| N-octyl lactobionamide | 2.3 mMol/L | 4.0% |
|   | 11.6 mMol/L | 24.0% |
| N-decyl lactobionamide | 4.0 mMol/L | 9.2% |
|   | 20.1 mMol/L | 14.9% |
| N-dodecyl lactobionamide | 3.8 mMol/L | 3.0% |
|   | 19.0 mMol/L | 3.8% |
| N-tetradecyl lactobionamide | 4.0 mMol/L | 1.0% |
|   | 20 mMol/L | 3.3% |
| N-(polyethyleneoxide) bis lactobionamide | 3.9 mMol/L | 22.2% |

*Latex bead-Bacterial Agglutination was performed as described above (Methods section) using *Actinomyces naeslundii* PK29.

As can be seen from Table 2, lactobionamide compounds also inhibited the β-galactose specific binding of *A. naeslundii* to glycoprotein coated latex beads. N-alkyl lactobionamides with relatively short carbon chains exhibited greater inhibitory activity than the parent saccharide, lactobionic acid.

As can be seen from Table 2, even lactobionamide compounds for which poor inhibitory activity was observed in Bacterial Coaggregation Assay, were found to be effective inhibitors of bacterial adhesion to glycoprotein coated surfaces in Latex Bead Assay.

Furthermore, these higher chain length compounds are valuable because, along with stereospecific targeting, they are capable of delivering surfactancy benefit (see Example 4) and antibacterial activity (see Example 6, Table 4).

Although not wishing to be bound by theory, it is believed that the reduced antiadhesion properties of the decyl, dodecyl, and tetradecyl lactobionamides compared to lower alkyl chain length lactobionamides is due to their decreased affinity for β-galactose specific bacterial binding proteins on *A. naeslundii*, which is possibly due to miscellar orientation of these compounds in the aqueous bacterial suspensions used in Bacterial Coaggregation Assay.

EXAMPLE 4

Several groups of the anti-plaque aldobionamide compounds employed in the inventive composition, for instance N-alkyl aldobionamides having an alkyl chain of greater than 8 carbon atoms, and N-alkyloxy alkyl lactobionamides included in the present compositions are capable of providing a surfactancy benefit, i.e. dispersing bacteria. For example, higher length N-alkyl aldobionamides had excellent foaming activity and their absorption to hydrophobic surfaces such as polystyrene was apparent during coaggregation and latex bead agglutination assay. The surfactant properties of various aldobionamides have been described in greater detail in a co-pending application, Ser. No. 07/816,419, filed Dec. 31, 1991, now abandoned; the examples of that application demonstrating the surfactant activity of lactobionamides are as follows:

Critical Micelle Concentration (CMC)

The CMC is defined as the concentration of a surfactant at which it begins to form micelles in solution. Specifically materials that contain both a hydrophobic group and a hydrophilic group (such as surfactants) will tend to distort the structure of the solvent (i.e., water) they are in and therefore increase the free energy of the system. They therefore concentrate at the surface, where, by orienting so that their hydrophobic groups are directed away from the solvent, the free energy of the solution is minimized. Another means of minimizing the free energy can be achieved by the aggregation of these surface-active molecules into clusters or micelles with their hydrophobic groups directed toward the interior of the cluster and their hydrophilic groups directed toward the solvent.

The value of the CMC is determined by surface tension measurements using the Wilhemy plate method. While not wishing to be bound by theory, it is believed that a low CMC is a measure of surface activity (i.e., lower CMC of one surfactant versus another indicates the surfactant with lower CMC is more surface active). In this regard, it is believed that lower CMC signifies that lesser amounts of a surfactant are required to provide the same surfactancy benefits as a surfactant with higher CMC.

The CMC of various surfactants were measured and the results set forth below:

| Surfactant | CMC |
|---|---|
| n-Dodecyl-β-D-glucoside | $1.9 \times 10^{-4}$ M (25° C.) |
| n-$C_{12}$ alcohol (with 7 EO's) | $7.3 \times 10^{-5}$ M (40° C.) |
| $C_{10}$-lactobionamide | — |
| $C_{12}$-lactobionamide | $4.2 \times 10^{-4}$ M (45° C.) |
| $C_{14}$-lactobionamide | $4.5 \times 10^{-5}$ M (45° C.) |

As the table above indicates, the CMC values of N-decyl and tetradecyl lactobionamides were found to be comparable to that of N-Dodecyl-β-D glucoside and heptaethoxylated dodecyl alcohol. These values indicate that the lactobionamide surfactants are comparable to other widely used nonionic surfactants.

Krafft Points

The temperature at and above which surfactants begin to form micelles instead of precipitates is referred to as Krafft point (Tk) and at this temperature the solubility of a surfactant becomes equal to its CMC.

Krafft point was measured by preparing a 1% dispersion of the surfactant in water. If the surfactant was soluble at room temperature, the solution was cooled to 0° C. When the surfactant did not precipitate out, its Krafft point was considered to be <0° C. If it precipitated out, the solution was slowly warmed with stirring in a water bath. The temperature at which the precipitate dissolved was determined to be the Krafft point.

If the Krafft point was above room temperature, the solution was first heated rapidly to dissolve all the surfactant. It was then cooled until precipitation occurred, and was then slowly warmed to determine the Krafft point described above.

While not wishing to be bound by theory, it is believed that lower Krafft points are indicative of a surfactant being more soluble in aqueous system.

The Krafft point of various lactobionamides is set forth as follows:

|  | Krafft Point |
|---|---|
| $C_{10}$-lactobionamide | 0° C. |
| $C_{12}$-lactobionamide | 38° C. |
| $C_{14}$-lactobionamide | 46° C. |

This table indicates that the $C_{10}$ chain length surfactants would tend to have better surfactancy properties than $C_{12}$ and $C_{14}$ counterparts at lower temperatures.

Foam Height

Since most of the foaming data on surfactants is typically obtained by the Ross-Miles method (Ross, J. and Miles, G. D., am. Soc. for Testing Material Method D1173-53 Philadelphia, Pa. (1953); Oil & Soap (1958) 62:1260) the foaming ability of these surfactants was also acquired using this method.

In the Ross-Miles method, 200 mL of a solution of surfactant contained in a pipette of specified dimensions with a 2.9-mm-i.d. orifice is allowed to fall 90 cm onto 50 mL of the same solution contained in a cylindrical vessel maintained at a given temperature (often 60° C.) by means of a water jacket. The height of the foam produced in the cylindrical vessel is read immediately after all the solution has run out of the pipette (initial foam height) and then again after a given amount of time (generally, 5 min).

Using this method, the foam production (measured initially) and foam stability (the height after 10 minutes) are reported. All of the foaming was achieved at 45° C. in water with 120 ppm hardness. The foam height is represented in millimeters (mm).

The initial foam height and height after 10 minutes (i.e. foam stability) for various surfactants and mixtures of surfactants is set forth below:

|                        | Initial Height | After 10 Minutes |
|------------------------|----------------|------------------|
| C$_{10}$ lactobionamide | 150            | 5                |
| C$_{12}$ lactobionamide | 160            | 6                |
| C$_{14}$ lactobionamide | 145            | 140              |
| Mixture of C$_{12}$ and C$_{14}$ | 155  | 135              |
| Neodol 91-6            | 130            | 5                |

TABLE 4

Minimum Inhibitory Concentrations (% w/v)

| Tested Compound | Streptococcus sanguis | Streptococcus sobrinus | Actinomyces naeslundii | Porphyromonas gingivalis | Prevotella intermedius | Veillonella dispar | Neisseria subflava | Candida albicans |
|---|---|---|---|---|---|---|---|---|
| Lactobionic acid | >0.5 | >0.5 | >0.5 | — | — | — | — | — |
| Decylgluconamide | >0.5 | >0.5 | >0.5 | — | — | — | — | — |
| Sodium dodecyl sulfate | 0.0015 | 0.006 | 0.0008 | 0.0002 | 0.0016 | 0.006 | 0.0008 | 0.006 |
| Propyl lactobionamide | >0.1 | >0.5 | >0.5 | >0.1 | >0.1 | >0.1 | >0.1 | >0.1 |
| Pentyl lactobionamide | >0.1 | >0.5 | >0.5 | >0.1 | >0.1 | >0.1 | >0.1 | >0.1 |
| Octyl lactobionamide | >0.1 | >0.5 | >0.5 | >0.1 | >0.1 | >0.1 | >0.1 | >0.1 |
| Decyl lactobionamide | >0.05 | >0.05 | >0.05 | — | >0.05 | 0.05 | 0.05 | 0.05 |
| Dodecyl lactobionamide | 0.0125 | 0.0125 | 0.006 | 0.003 | 0.025 | 0.006 | 0.025 | 0.0125 |
| Tetradecyl lactobionamide | 0.003 | 0.0125 | 0.0015 | — | 0.0008 | <0.0008 | 0.006 | 0.003 |
| Hexadecyl lactobionamide | 0.0125 | 0.1 | 0.006 | >0.05 | >0.05 | >0.05 | 0.1 | 0.1 |
| Dodecyl-B-alanyl-lactobionamide | 0.0125 | 0.1 | 0.0125 | — | — | — | 0.05 | 0.05 |
| Tetradecyl-glycyl-lactobionamide | 0.003 | 0.05 | 0.0008 | — | — | — | 0.05 | 0.05 |
| Dodecyl ammonium lactobionate | 0.006 | 0.003 | 0.003 | — | 0.0016 | 0.0016 | 0.0125 | — |
| Tetradecyl ammonium Lactobionate | 0.0016 | 0.0125 | 0.006 | — | — | — | — | 0.0125 |

As seen above, the C$_{14}$ lactobionamide and the mixture of C$_{12}$ and C$_{14}$ lactobionamides shows best foam stability.

It should be noted that it is very unusual to get this type of foam stability with other nonionics.

EXAMPLE 5

Alkyl ammonium salts of lactobionic acid were also tested for their effects on bacterial coaggregation. As shown in Table 3, tetadecylammonium lactobionate was an effective inhibitor of coaggregation between *A. naeslundii* and *S. sanguis*, causing inhibition at relatively low concentrations. Dodecyl- and tetradecylammonium lactobionate also exhibited significant anti-microbial activity as determined in MIC assays performed on several species of oral bacteria (Example 6). It should be noted that tetradecyl ammonium hydrochloride also inhibited coaggregation and had antibacterial activity.

TABLE 3

Inhibition of coaggregation of *A. naeslundii* and *S. sanguis* by tetradecyl lactobionate*

| Tetradecyl lactobionate Concentration | Percent Inhibition # |
|---|---|
| 0.5 mMol/L | 0.0% |
| 0.7 mMol/L | 11% |
| 0.9 mMol/L | 66% |
| 1.4 mMol/L | 99% |
| 1.8 mMol/L | 100% |

*Coaggregation of *Actinomyces naeslundii* PK29 and *Streptococcus sanguis* G9B performed as described above.
% Inhibition calculated as 1.0 - the change in optical density (540 nm) in the sample containing the inhibitor/the change in optical density in the coaggregation buffer control.

EXAMPLE 6

Various aldobionamides were tested for their bacteriostatic effects on the growth of several species of oral bacteria. As shown in Table 4, many N-alkyl lactobionamides displayed considerable anti-bacterial activity. In several instances, the anti-bacterial activity of these compounds approached that observed for the anionic surfactant, sodium dodecyl sulfate. Therefore, many of these molecules can deliver multiple anti-plaque benefits including anti-microbial activity, targeting to stereospecific bacterial binding proteins, and where applicable, surface-active properties.

EXAMPLE 7

A typical toothpaste formula containing the aldobionamide plaque inhibitor of the present invention is as follows:

Toothpaste Formula (pH = 5-9)

| Component | Percent by Weight of the Final Composition |
|---|---|
| 70% Sorbitol | 64.0% |
| Abrasive Silica | 10.0% |
| Thickening Silica | 9.0% |
| Aldobionamide Antiplaque Agent | 5.0% |
| Polyethylene Glycol | 5.0% |
| Sodium Dodecyl Sulfate | 1.5% |
| Flavor | 1.0% |
| Sodium Saccharinate | 0.3% |
| Sodium Fluoride | 0.24% |
| Preservative (Benzoate) | 0.08% |
| Dye | <.01% |
| Sodium Carboxymethyl Cellulose | 0.15% |
| Water | to 100% |

EXAMPLE 8

A typical formula for a mouthwash containing the aldobionamide antiplaque agents of the present invention is as follows:

Mouthwash Formula (pH = 6.5)

| Component | Percent by Weight of Final Composition |
|---|---|
| Ethanol | 12.5% |
| 70% Sorbitol | 7.0% |
| Aldobionamide Anti-plaque Agent | 5.0% |
| Tween 20 | 0.55% |
| Preservatives (parabens) | 0.2% |
| Flavor | 0.1% |
| Dye | <.1% |

-continued

Mouthwash Formula (pH = 6.5)

| Component | Percent by Weight of Final Composition |
| --- | --- |
| Sodium Saccharinate | 0.65% |
| Sodium Chloride | 0.05% |
| Sodium Acetate | 0.015% |
| Acetic Acid | 0.015% |
| Water | to 100% |

Some suppliers for the materials employed in the invention have been mentioned in the description. Other materials in the description of the invention are available from the following suppliers:

| Material | Supplier |
| --- | --- |
| Bacteria: | |
| a) *Streptococcus sangius* G9B | In-house culture collection |
| b) *Actinomyces naeslundii* PK29 | Paul Kollenbrander, NIH, Bethes |
| c) *Candida albicans* GR12773 | R. Santarpia, SUNY, Stony Brook NY |
| d) *Neisseria subflava* A1078 | Phil Marsh, PHLS (centre for Applied Microbiology, Porton Down, UK) |
| e) *Porphyromonas gingivalis* W83 | Phil Marsh, PHLS (centre for Applied Microbiology, Porton Down, UK |
| f) *Veillonella dispar* 17745 | In-house culture collection |
| g) *Streptococcus sobrinus* 6715 | In-house culture collection |
| h) *Prevotella intermedia* 25611 | In-house culture collection |
| 6.0 mM diameter styreme divinyl benzene Latex Beads | Sigma |
| Lactobionic acid-hemi calcium salt | Sigma |
| Lactose | BBL - Becton Dickinson |
| Galactose | Fisher |
| Bovine Serum Albumin | Sigma |
| Asialofetuin | Sigma |
| Tween 20 ® (polysorbate 20) | ICI Americas Inc. |
| Plastic cuvettes - 4-5 ml polystyrene | Disposlab Kartell |
| Tryptone | Difco |
| Yeast Extract | BBL - Becton Dickinson |
| Beef Heart Infusion Broth | BBL - Becton Dickinson |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. An oral hygiene composition comprising a suitable carrier and an effective plaque-inhibiting amount of at least one compound selected from the group consisting of an aldobionamide and a corresponding ammonium salt of aldobionic acid, wherein the compound includes (i) at least one β-galactosidic linkage and (ii) an amide group:

wherein $R^1$ and $R^2$ are the same or different and are selected from the group consisting of hydrogen, an aliphatic hydrocarbon radical, an aromatic radical, a cycloaliphatic radical, an amino acid ester and mixtures thereof.

2. The composition of claim 1 wherein $R^1$ and $R^2$ are the same or different and contain a heteroatom selected from the group consisting of nitrogen, oxygen, and sulphur.

3. The composition of claim 1 wherein $R^1$ is hydrogen.

4. The composition of claim 3 wherein $R^2$ is an aliphatic hydrocarbon radical selected from the group consisting of a saturated and an unsaturated radical, branched and straight radicals.

5. The composition of claim 1 wherein $R^1$ and $R^2$ are the same or different and both together include from 1 to 36 carbon atoms.

6. The composition of claim 1 wherein $R^1$ is hydrogen and $R^2$ is an aliphatic hydrocarbon radical containing from 1 to 36 carbon atoms.

7. The composition of claim 1 wherein the aldobionamide is a lactobionamide of Formula A

FORMULA A

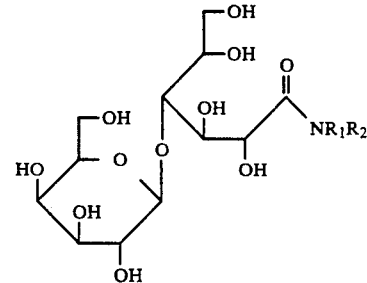

wherein $R^1$ and $R^2$ are the same or different and are selected from the group consisting of hydrogen, an aliphatic hydrocarbon radical, an aromatic radical, a cycloaliphatic radical, an amino acid ester and mixtures thereof.

8. The composition of claim 1 wherein the composition comprises an ammonium salt of lactobionic acid.

9. The composition of claim 7 wherein $R^1$ and $R^2$ are the same or different and contain a heteroatom selected from the group consisting of nitrogen, oxygen, and sulphur.

10. The composition of claim 7 wherein $R^1$ is hydrogen.

11. The composition of claim 10 wherein $R^2$ is an aliphatic hydrocarbon radical selected from the group consisting of a saturated and an unsaturated radical, branched and straight radicals.

12. The composition of claim 7 wherein $R^1$ and $R^2$ are the same or different and both together include from 1 to 36 carbon atoms.

13. The composition of claim 7 wherein $R^1$ is hydrogen and $R^2$ is an aliphatic hydrocarbon radical containing from 1 to 36 carbon atoms.

14. The composition of claim 7 wherein at least one compound of Formula A is an N-alkyl lactobionamide, wherein R1 and R2 contain a total of from 8 to 18 carbon atoms.

15. The composition of claim 7 wherein the lactobionamide has an alkyl chain having from 1 to 8 carbon atoms.

16. The composition of claim 7 wherein $R^1$ is hydrogen and $R^2$ is an ester of an amino acid.

17. The composition of claim 7 wherein at least one compound of Formula A is an N-(alkyloxy) alkyl lactobionamide, wherein $R^1$ is hydrogen, $R^2$ is —(CH$_2$-

$)_n$—O—R$^3$, wherein n is an integer equal to or greater than 1 and R$^3$ is an alkyl radical.

18. The composition of claim 17 wherein the value of n and the number of carbon atoms in the alkyl radical R$^3$ is such that R$^2$ contains from 2 to 36 carbon atoms.

19. The composition of claim 17 wherein n is an integer from 1 to 10.

20. The composition of claim 17 wherein at least one compound of Formula A is an N-(polyalkyloxy)alkyl lactobionamide.

21. The composition of claim 20 wherein R$^1$ and/or R$^2$ is —R$^4$—(OR$^4$)$_n$—R$^4$—R$^5$ wherein n is an integer equal to or greater than 1, R$^4$ is selected from the group consisting of ethylene, propylene, and mixtures thereof; and R$^5$ is an amine or lactobionate moiety.

22. The composition of claim 21 wherein n is an integer from 2 to 10,000 and R$^5$ is lactobionate.

23. The composition of claim 1 wherein the compound is employed in the amount of at least 0.0001%.

24. The composition of claim 7 wherein the compound is employed in the amount of at least 0.0001%.

25. The composition of claim 1 wherein the composition further comprises a source of fluoride ion.

26. The composition of claim 7 wherein the composition further comprises a source of fluoride ion.

27. The composition of claim 1 wherein the composition further comprises a source of zinc ion.

28. The composition of claim 7 wherein the composition further comprises a source of zinc ion.

29. A method of inhibiting plaque growth in an oral cavity comprising applying into the oral cavity a composition comprising an effective plaque-inhibiting amount of at least one compound selected from the group consisting of an aldobionamide and a corresponding ammonium salt of aldobionic acid, wherein the aldobionamide includes (i) at least one β-galactosidic linkage and (ii) an amide group:

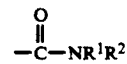

wherein R$^1$ and R$^2$ are the same or different and are selected from the group consisting of hydrogen, an aliphatic hydrocarbon radical, an aromatic radical, a cycloaliphatic radical, an amino acid ester and mixtures thereof.

* * * * *